US010933201B2

(12) United States Patent
Lam (10) Patent No.: US 10,933,201 B2
(45) Date of Patent: Mar. 2, 2021

(54) DRUG DELIVERY DEVICE AND PREDETERMINED BREAKING MEMBER FOR A DRUG DELIVERY DEVICE (71) Applicant: SANOFI-AVENTIS DEUTSCHLAND GMBH, Frankfurt am Main (DE)

(72) Inventor: Ngoc-Jane Lam, Frankfurt am Main (DE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 504 days.

(21) Appl. No.: 15/567,625

(22) PCT Filed: Apr. 20, 2016

(86) PCT No.: PCT/EP2016/058686
§ 371 (c)(1),
(2) Date: Oct. 19, 2017

(87) PCT Pub. No.: WO2016/169944
PCT Pub. Date: Oct. 27, 2016

(65) Prior Publication Data
US 2018/0085537 A1 Mar. 29, 2018

(30) Foreign Application Priority Data

Apr. 23, 2015 (EP) .................................... 15164813

(51) Int. Cl.
A61M 5/50 (2006.01)
A61M 5/315 (2006.01)
A61M 5/31 (2006.01)

(52) U.S. Cl.
CPC ...... *A61M 5/5066* (2013.01); *A61M 5/31551* (2013.01); *A61M 2005/3126* (2013.01); *A61M 2005/5073* (2013.01)

(58) Field of Classification Search
CPC ...... A61M 5/31551; A61M 2005/5073; A61M 5/5066; A61M 5/31576; A61M 2005/3126
See application file for complete search history.

(56) References Cited

U.S. PATENT DOCUMENTS 5,573,514 A * 11/1996 Stiehl ...................... A61M 5/24
604/198
6,620,135 B1 * 9/2003 Weston ............... A61M 5/2053
604/140
(Continued)

FOREIGN PATENT DOCUMENTS

CN 201862083 6/2011
EP 1935444 6/2008
(Continued)

OTHER PUBLICATIONS

International Preliminary Report on Patentability in Application No. PCT/EP2016/058686, dated Oct. 24, 2017, 7 pages.
(Continued)

*Primary Examiner* — Theodore J Stigell
(74) *Attorney, Agent, or Firm* — Fish & Richardson P.C.

(57) ABSTRACT

A drug delivery device comprises a housing and a mechanical assembly, which is at least partially accommodated in the housing. The mechanical assembly comprises a predetermined breaking member, which is configured to be damaged when forcefully separated from the housing.

16 Claims, 2 Drawing Sheets (56) References Cited

U.S. PATENT DOCUMENTS

| | | | |
|---|---|---|---|
| 2002/0055712 A1 | 5/2002 | Neracher | |
| 2003/0212366 A1* | 11/2003 | Bang .................... | A61M 5/322 |
| | | | 604/196 |
| 2008/0045899 A1* | 2/2008 | Wu ....................... | A61M 5/322 |
| | | | 604/110 |
| 2008/0262437 A1* | 10/2008 | Hirschel ........... | A61M 5/31535 |
| | | | 604/207 |
| 2009/0048560 A1* | 2/2009 | Caizza ................ | A61M 5/5066 |
| | | | 604/110 |
| 2015/0018775 A1* | 1/2015 | Groeschke ........ | A61M 5/31568 |
| | | | 604/207 |
| 2015/0051544 A1* | 2/2015 | Sendatzki ............ | A61M 5/502 |
| | | | 604/110 |

FOREIGN PATENT DOCUMENTS

| | | |
|---|---|---|
| JP | H1-24838 | 1/1990 |
| JP | 2012-509736 | 4/2012 |
| WO | WO 2004/078239 | 9/2004 |
| WO | WO 2010/062393 | 6/2010 |

OTHER PUBLICATIONS

International Search Report and Written Opinion in International Application No. PCT/EP2016/058686, dated Jun. 29, 2016, 9 pages.

* cited by examiner

DRUG DELIVERY DEVICE AND PREDETERMINED BREAKING MEMBER FOR A DRUG DELIVERY DEVICE

CROSS REFERENCE TO RELATED APPLICATIONS

The present application is the national stage entry of International Patent Application No. PCT/EP2016/058686, filed on Apr. 20, 2016, and claims priority to Application No. EP 15164813.6, filed in on Apr. 23, 2015, the disclosures of which are expressly incorporated herein in entirety by reference thereto.

TECHNICAL FIELD

The present disclosure relates to a drug delivery device, for example to an injection device.

BACKGROUND

A drug delivery device may be designed as the device disclosed in patent application WO 2004/078239 A1.

A disposable device is configured to be disposed when a drug reservoir is empty. Such a drug delivery device may also be referred to as a non-refillable or non-reusable device as the device may not be configured to be refilled and/or reused with a refilled drug. Refilling may mean exchanging an empty drug reservoir with a drug reservoir containing a drug or may mean refilling an empty drug reservoir with a drug.

Although disposable devices may not be meant to be refilled, manipulated devices have come on the market. Often, the refilled drug in such a manipulated device, is not identical to the drug originally contained in the device. As an example, the refilled drug in the manipulated device may be a diluted form of the original drug. The diluted drug may be non-discernable for a user from the original drug, which may pose a considerable health risk to the user.

SUMMARY

According to a first aspect, a drug delivery device comprises a housing and a mechanical assembly, which is at least partially accommodated in the housing. The drug delivery device may comprise a piston rod. The mechanical assembly may be configured to drive the piston rod forwards for dispensing a dose of a drug. During the use of the device, in particular in a dispense operation, the piston rod and/or parts of the mechanical assembly may move from a start position towards an end position in the device. The start position may be a most proximal position of the respective member relative to the housing. Furthermore, the mechanical assembly may be configured to set a size of a dose to be dispensed. Setting the dose may comprise selecting the size of a dose and/or preparing the mechanical assembly for a dispense operation.

The drug delivery device may be an injection device, in particular a pen-type injection device. The device may comprise a drug reservoir, in particular a cartridge. The drug reservoir may be configured to be mounted at a distal end of the housing. The term "distal end" may describe an end of the device or a part thereof which is closest to a dispensing end of the device. The term "proximal end" may describe an end of the device or a part thereof which is furthest away from the dispensing end of the device. Analogously, the term "distal direction" may describe a direction towards a dispensing end of the device and the term "proximal direction" may describe a direction away from the dispensing end of the device.

The drug delivery device may be a non-reusable device. As an example, the device may be configured for not supporting a dismounting of a drug reservoir. The drug reservoir may only be forcefully dismounted from the housing. A reuse of the device may further require a reset of the mechanical assembly and/or a piston rod to a start position in the device. The drug delivery device may be configured for not supporting such a reset. For example, the drug delivery device may be configured for not supporting a removal of the mechanical assembly from the housing which may be required for resetting the device. As an example, the drug delivery device may comprise a stop for stopping the mechanical assembly from being completely drawn out of the housing. However, although the device may not be configured and intended to be reused, a user may try to forcefully disassemble the device, refill the drug and reset components of the device to their respective start positions.

The mechanical assembly comprises a predetermined breaking member configured to be damaged when the mechanical assembly or parts thereof are forcefully separated from the housing. In particular, the predetermined breaking member may be configured to be damaged when the predetermined breaking member is forcefully separated from the housing. The predetermined breaking member may be damaged such that the predetermined breaking member is cracked, is partially or completely broken, and/or is deformed. Preferably, the predetermined breaking member is configured to prevent a reuse of the device once the mechanical assembly or parts thereof have been disassembled from the housing. In particular, the damage of the predetermined breaking member that occurs during forceful separation may prevent proper functioning of the mechanical assembly and/or may prevent correctly re-assembling the device. However, the predetermined breaking member is preferably stable such that it is not damaged during normal use of the device, e.g., during dose setting or dispense.

The predetermined breaking member may be configured to partially protrude out of and/or into the housing during normal use of the device, in particular during dose setting and/or dose dispense. Accordingly, the user may access the predetermined breaking member from an outside portion of the drug delivery device. When trying to disassemble the mechanical assembly from the housing, the predetermined breaking member may be gripped by a user and forcefully drawn completely out of the housing. For example, the predetermined breaking member may abut at a stop configured to prevent the predetermined breaking member from being completely drawn out of the housing. Large bending and/or axial forces may be applied to the predetermined breaking member to draw the predetermined breaking member out of the housing and to overcome the stop. Together with the predetermined breaking member, further parts of the mechanical assembly may be drawn out of the housing.

The predetermined breaking member may have the shape of a sleeve. During dose setting, the predetermined breaking member may move further out of the housing. During dose dispense, the predetermined breaking member may move towards the housing.

For example, the predetermined breaking member may be configured as an indicator member for displaying information to the user. In particular, the indicator member may be configured to display the size of a dose of a drug to be dispensed. The indicator member may comprise indications, in particular numbers. An indication indicating the size of a set dose or other information related to the current status of the device may be visible in a dose display, in particular through an opening in the housing.

The predetermined breaking member comprises a predetermined breaking region at which the predetermined breaking member is configured to be damaged during disassembly from the housing. Accordingly, the predetermined breaking region is a defined weak point or region of the predetermined breaking member. In particular, the predetermined breaking region may be a region having a reduced mechanical stability compared to further regions of the predetermined breaking member.

In an embodiment, the predetermined breaking region comprises at least one spot having a reduced thickness of material or being configured as a perforation. The at least one spot may have a point-shaped geometry or a dash-shaped geometry, for example. As an example, the at least one spot may be configured as a slit.

The predetermined breaking region may comprise several such spots. As an example, the spots may be arranged in a line. In this case, a crack may occur along the line during forceful separation of the predetermined breaking member from the housing. The line of spots may run around a circumference of the predetermined breaking member. As an example, the line may run as a closed line around a circumference of the predetermined breaking member. As a further example, the line of spots may run helically around a circumference of the predetermined breaking member.

The predetermined breaking member may comprise a thread. The predetermined breaking member may be threadedly engaged with the housing or a part fixed to the housing during normal use of the device. The predetermined breaking region may be located in a groove of the thread. As an example, the predetermined breaking region may comprise a line of spots as described above, wherein the line of spots is located in the groove.

Preferably, the predetermined breaking region does not extend along the whole length of the predetermined breaking member. For example, the predetermined breaking region may only be located along a section of the groove. The predetermined breaking region may be located in a distal section of the predetermined breaking member. The predetermined breaking region may be located in a section of the predetermined breaking member which is in direct engagement with the housing. Alternatively, the predetermined breaking region may be located in a section that is fixed to the housing when a user tries to manipulate the device. Manipulation of the device may apply large forces to the section, thus the section is most prone to be damaged.

In an embodiment, the predetermined breaking region is configured to be non-visible from outside the drug delivery device. In particular, the predetermined breaking region is not visible at least as long as the predetermined breaking member is partially accommodated in the housing. Thus, some embodiments are configured such that a user may not be aware of the predetermined breaking region.

For example, the predetermined breaking region may be located only in a part of the member which is always covered by the housing or other parts of the device as long as the predetermined breaking member is assembled with the housing. The predetermined breaking region may be located near the distal end of the predetermined breaking member.

In a further example, an outer surface of the predetermined breaking member in the predetermined breaking region may be non-discernable from an outer surface in a more stable region of the predetermined breaking member. A more stable region is a region having higher mechanical stability than the predetermined breaking region. In other words, the predetermined breaking region may be designed such that a user may not be able to detect the existence of a predetermined breaking region even if the predetermined breaking region is not covered by the housing or other parts of the device. For example, the predetermined breaking region may comprise at least one spot having a reduced thickness of material wherein the reduced thickness of material may not be visible from outside. In particular, the spot may be an indentation in an inner surface of the predetermined breaking member which does not extend to the outer surface of the predetermined breaking member.

In this case, the predetermined breaking region may be located in a part of the predetermined breaking member which protrudes out of the housing during normal use of the device. As an example, the predetermined breaking region may start near the distal end of the device and may extend up to two thirds of the entire length of the predetermined breaking member.

According to an embodiment, the predetermined breaking member is configured as an indicator member for displaying the size of a dose of a drug to be dispensed. In particular, the indicator member may be a number sleeve. The indicator member may comprise a thread being engaged with the housing or a part fixed to the housing. The part fixed to the housing may be a housing insert, for example. The predetermined breaking region may be located inside a groove of the thread. Furthermore, the drug delivery device may comprise a stop configured to prevent the indicator member from being completely drawn out of, in particular wound out of, the housing. The stop may be a maximum dose stop for preventing a dose from being set which is larger than the amount of the drug left in the drug reservoir. As an example, the predetermined breaking member may be configured to abut the stop when the maximum dose is being set. Thereby, the predetermined breaking member may be stopped from being completely drawn out of the housing. However, a forceful separation may be possible, which may lead to a damage of the predetermined breaking member in the predetermined breaking region.

In certain aspects, a predetermined breaking member for a mechanical assembly of a drug delivery device is disclosed. The predetermined breaking member is configured to be damaged when being forcefully separated from the housing of the device. The predetermined breaking member may have all structural and functional properties as disclosed above. As an example, the predetermined breaking member may be configured as an indicator member for the drug delivery device. The predetermined breaking member may have a predetermined breaking region comprising one or more spots having a reduced thickness of material or being configured as a perforation. The spots may be located along a line running helically around a circumference of the predetermined breaking member.

The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36,Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

DETAILED DESCRIPTION

Like elements, elements of the same kind and identically acting elements may be provided with the same reference numerals in the figures.

Figure 1:
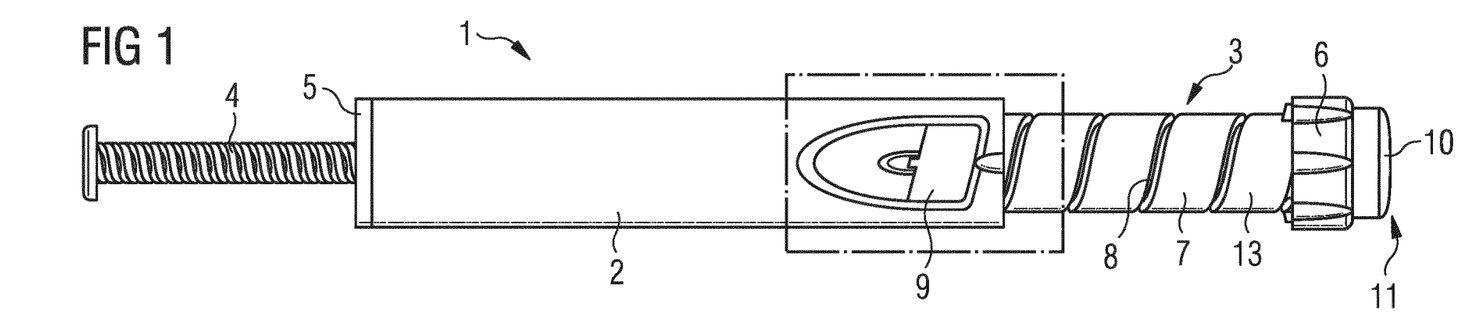
FIG. 1 shows a side view of a drug delivery device in an assembled state.

FIG. 1 shows a drug delivery device 1. The drug delivery device 1 is an injection device, in particular a pen-type injection device. The drug delivery device may be basically designed as the device disclosed in patent application WO 2004/078239 A1.

The drug delivery device 1 is a variable dose device such that a user can select the size of a dose. Alternatively, the drug delivery device 1 may be a fixed-dose device, i.e., a device wherein the size of a dose is fixed such that a user cannot select the size of the dose. The drug delivery device 1 may be configured for multiple dose applications. In this case the user may dispense multiple doses from the device, i.e. use the device in several dose dispense operations.

The drug delivery device 1 comprises a housing 2, in which a mechanical assembly 3 is partially accommodated. The mechanical assembly 3 may be configured to drive a piston rod 4 forwards for expelling a drug from a drug reservoir (not shown). The piston rod 4 may be configured as a lead screw. The piston rod 4 may be threadedly connected with the housing 2, for example by a part fixed to the housing 2. The drug may comprise insulin. The drug reservoir may be mounted to a distal end 5 of the housing 2. The drug reservoir may be configured as a cartridge. The cartridge may be accommodated in a cartridge holder. The drug reservoir may comprise a bung which is configured to be moved forwards by the piston rod 4.

The drug delivery device 1 comprises an indicator member 7 for displaying information about the status of the device 1, in particular the size of a set dose. A dose setting member 6 is fixed to the indicator member 7. The indicator member 7 comprises a thread 8 for threadedly connecting the indicator member 7 to the housing 2. The indicator member 7 may be directly engaged with the housing 2, in particular, to an outer housing of the device 1, or may be engaged with a part fixed to the housing 2. On its outer surface, the indicator member 7 comprises indications (not shown here), for example numbers, for indicating the size of the set dose.

For setting a dose, the dose setting member 6 may be rotated. Thereby, a desired size of a dose is set and/or the mechanical assembly 3 may be prepared for a subsequent dispense operation. When setting the dose, the dose setting member 6 and the indicator member 7 may move further out of the housing 2, in particular the dose setting member 6 and indicator member 7 may translate helically out of the housing 2. The size of the selected dose may be visible in a dose display 9. In particular, the dose display 9 may comprise an opening in the housing 2 through which a part of the indicator member 7 is visible. The indication on the indicator member 7 visible in the dose display 9 may correspond to the selected dose.

When the desired dose has been set, the user may then dispense the dose by depressing a dose button 10 at the proximal end 11 of the device 1. Thereby, the indicator member 7 moves back into the housing 2 and the piston rod 4 is advanced by the mechanical assembly 3 in a distal direction. Thereby, the piston rod 4 may drive a bung in a cartridge forwards to dispel a dose from the cartridge. Before the first use of the device 1, the piston rod 4 is located at a start position, which may be the most proximal position of the piston rod 4 relative to the housing. When a dose is dispensed from the device 1, the piston rod 4 moves distally. When all doses have been dispensed from the device, the piston rod 4 arrives at an end position, which may be the most distal position relative to the housing 2. Likewise, the mechanical assembly 3 or parts thereof may have a start position and an end position.

The drug delivery device 1 is a disposable device, i.e., the device 1 is meant to be disposed when the drug reservoir is empty. The drug delivery device 1 is not designed for being refilled and reused with a refilled drug. Refilling may include exchanging an empty cartridge for a new cartridge or may include refilling a drug in an empty cartridge. Refilling and reusing the device 1 may require the user to reset of the piston rod 4 and/or the mechanical assembly 3 to their respective start positions. Such a reset may only be possible when the mechanical assembly 3 or parts thereof are disassembled from the housing 2.

Although the device 1 is not designed for a removal of the mechanical assembly 3, a forceful removal may be possible by applying axial and/or bending forces to the mechanical assembly 3, in particular to the indicator member 7. The indicator member 7 may be screwed out of the housing 2 until further proximal movement is prevented by a stop feature of the device 1. Then, by manipulations in the region of the dose display 9, as indicated by the dotted box, mechanical forces may be transferred from the indicator member 7 to the housing 2. When the applied force exceeds a mechanical stability of the housing 2, the housing 2 may be deformed and the indicator member 7 may disconnect from the housing 2. The mechanical assembly 3 may be connected to the housing 2 only via the indicator member 7 such that a disconnection of the indicator member 7 may result in a disconnection of the mechanical assembly 3 from the housing 2. Furthermore, the force applied on the indicator member 7, 3 may also be disengaged the mechanical assembly from the piston rod 4. Thereby, the indicator member 7 and the mechanical assembly 3 may be forcefully disassembled from the housing 2.

Figure 2:
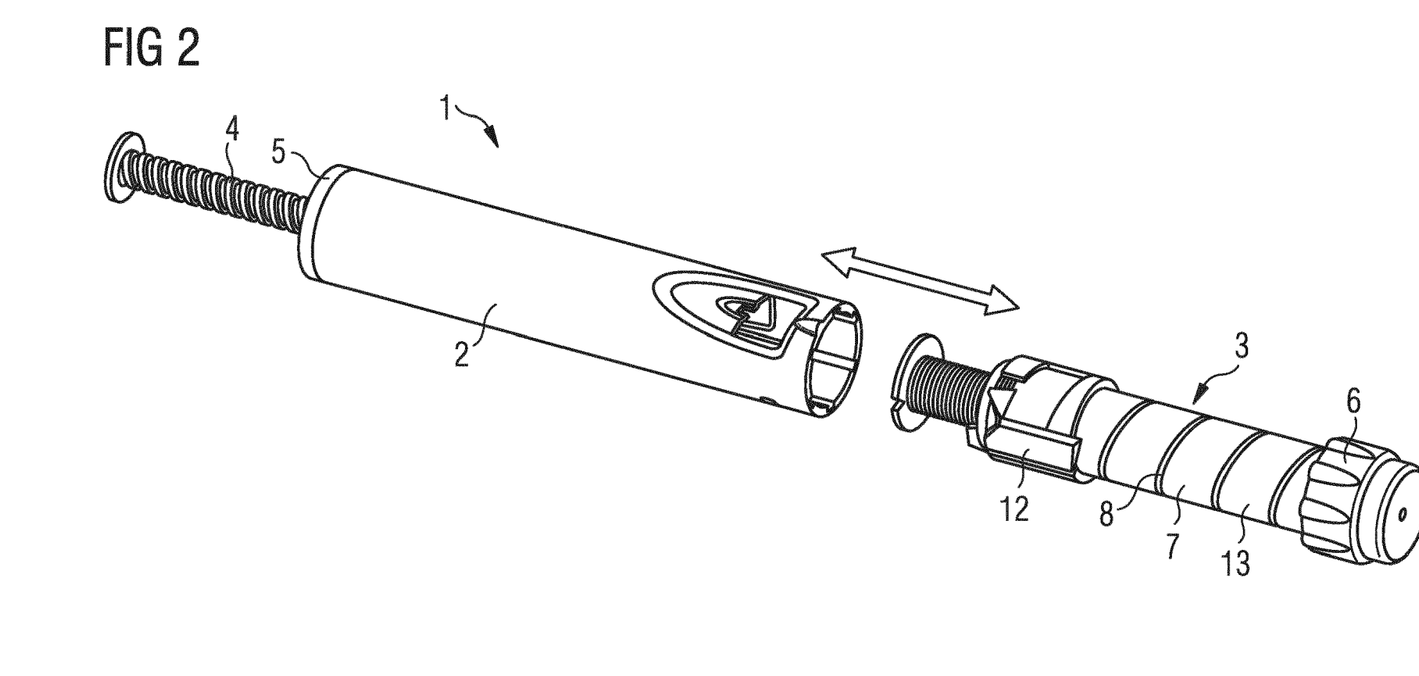
FIG. 2 shows a perspective view of the drug delivery device of FIG. 1 in a disassembled state.

FIG. 2 shows the device 1 of FIG. 1 with the mechanical assembly 3 having been forcefully removed from the housing 2. The indicator member 7 has been forced out of the housing 2 with a threaded insert 12. The threaded insert 12 is threadedly engaged with the thread 8 of the indicator member 7. The threaded insert 12 is fixed to the housing 2 and, thereby, threadedly connects the indicator member 7 with the housing 2 in the assembled state of the device 1 as shown in FIG. 1.

The drug delivery device 1 may be configured such that the reuse of the device 1 is prevented once the mechanical assembly 3 or parts thereof have been forcefully removed from the housing 2. The drug delivery device 1 comprises a predetermined breaking member 13 which is configured to be damaged, such that the predetermined breaking member 13 is broken when the mechanical assembly 3 or parts thereof are forced out of the housing 2. Preferably, damaging the predetermined breaking member 13 prevents the reset and/or the reuse of the device 1.

For example, the indicator member 7 may be configured as the predetermined breaking member 13. Alternatively or additionally, other parts of the mechanical assembly 3 may be configured as the predetermined breaking member 13.

Figure 3:
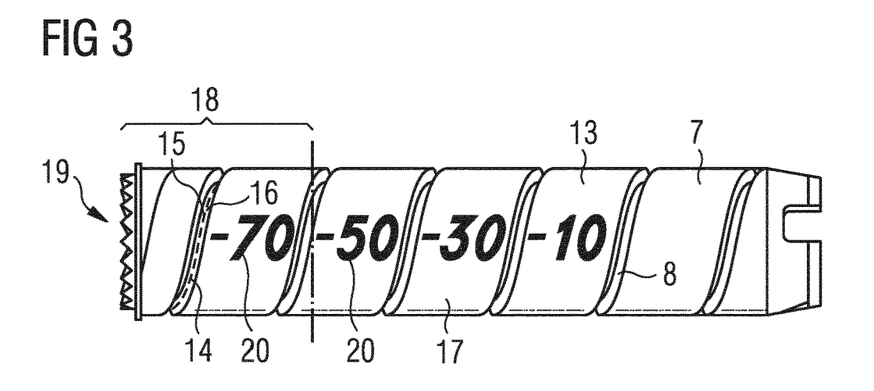
FIG. 3 shows a side view of a predetermined breaking member according to an embodiment.

FIG. 3 shows an embodiment of a predetermined breaking member 13 embodied as an indicator member 7. The predetermined breaking member 13 comprises a predetermined breaking region 14, in which the predetermined breaking member 13 is configured to be damaged when the predetermined breaking member 13 is forcefully separated from the housing 2, for example when the predetermined breaking member 13 is forcefully drawn or rotated out of the housing 2. The damage of the predetermined breaking member 13 may prevent restoration of the mechanical function of the device 1. The predetermined breaking region 14 is a region with reduced mechanical stability compared to other regions of the member 13. For example, the predetermined breaking region 14 comprises one or more spots 15 having a reduced thickness of material or a perforation.

For example, the predetermined breaking region 14 may helically extend along the indicator member 7. The predetermined breaking region 14 may be located in a groove 16 of a thread 8 of the predetermined breaking member 13. The predetermined breaking region 14 may not extend along the entire thread 8. The thread 8 comprises stable regions 17 which are not mechanically weakened.

Preferably, the predetermined breaking region 14 of the indicator member 7 is not visible from the outside of the housing 2. As an example, the predetermined breaking region 14 may be located at a part 18 of the predetermined breaking member 13, which is not visible from outside when the device 1 is in its assembled state as shown in FIG. 1. In particular, the predetermined breaking region 14 may be located only near a distal end 19 of the indicator member 7. The distal end 19 may be accommodated in the housing 2 in the assembled state of the device 1. Preferably, the predetermined breaking region 14 is not visible through the dose display 9. In particular, the predetermined breaking region 14 may be always covered by a part of the housing 2 when assembled with the housing 2. When manipulating the drug delivery device 1, the largest strain may be imposed near the distal end 19 of the indicator member 7. Therefore, providing the distal end 19 of the indicator member 7 with the predetermined breaking region 14 will most effectively lead to a damage of the indicator member 7.

For example, the indicator member 7 may comprise indications 20, in particular numbers, for indicating the size of a selected dose in the dose display 9. The maximum dose to be set may be 80 Units indicated by the number "80" (not shown). When manipulating the device 1, the indicator member 7 may first be rotated out of the housing 2 until a stop position is reached. The stop position may be a position of the indicator member 7 at which the 80 units are indicated. The predetermined breaking region 14 may be located between the 80 Units indication and a 54 Units indication. A part 18 of the distal end of the indicator member 7 that includes the predetermined breaking region 14 may always be accommodated in the housing 2 during normal use of the drug delivery device 1.

Figure 4:
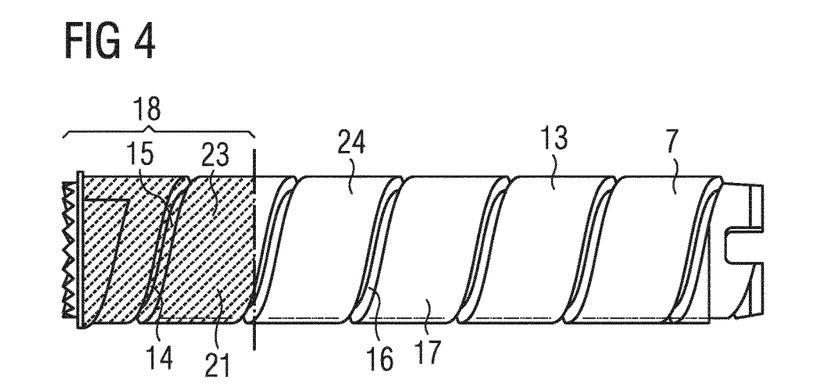
FIG. 4 shows a side view of a predetermined breaking member according to a further embodiment.

FIG. 4 shows a further embodiment of a predetermined breaking member 13. In contrast to the embodiment shown in FIG. 3, the predetermined breaking region 14 is not discernable from further parts of the predetermined breaking member 13 even when not covered by the housing 2 of the device 1.

As an example, the predetermined breaking region 14 may comprise spots 15 being configured as perforations or having a reduced material thickness, wherein the spots 15 are covered by a covering material 21 of the predetermined breaking member 13. The spots 15 may be referred to as closed perforations. As an example, the spots may be configured as one or more indentations in an inner surface area of the predetermined breaking member 13. In particular, the predetermined breaking member 13 may comprise a sleeve, wherein an inner surface of the sleeve comprises the indentations. Preferably, the indentations do not extend to the outer surface 23 of the sleeve. The spots 15 may be located in the groove 16 as shown in FIG. 3 or in other areas of the predetermined breaking member 13.

Because an outer surface 23 in the predetermined breaking region 14 is not discernable from an outer surface 24 in a stable region of the predetermined breaking member 13, the predetermined breaking region 14 may also be located in a part of the member 13 which is visible from the outside. For example, the predetermined breaking region 14 may be located in a part 22 which may protrude out of the housing 2 during the normal use of the device 1.

A further advantage of a predetermined breaking region 14 configured without open perforations is a reduction in loss of lubrication grease, which may be applied to the predetermined breaking member 13.

Figure 5:
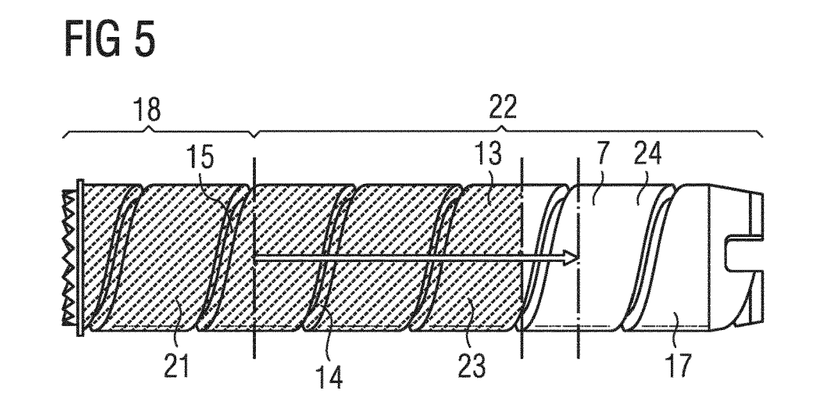
FIG. 5 shows a side view of a predetermined breaking member according to a further embodiment.

FIG. 5 shows a predetermined breaking member 13 similar to the one shown in FIG. 4. In FIG. 5 the predetermined breaking region 14 extends further in proximal direction. As indicated by the arrow and the dotted lines, the predetermined breaking region 14 may extend axially up to about three-fourths of the total length of the predetermined breaking member 13. For example, the predetermined breaking region 14 may extend in a section 22 of the indicator member 7 which may protrude out of the housing 2 during normal use of the device. Accordingly, during manipulation, damage of the predetermined breaking member 13 may occur near the distal end of the member 13 and at further parts of the member 13.

The predetermined breaking member 13 as shown in FIGS. 1 to 5 may be produced in an injection molding process. In particular, a plastic material may be used for producing the components. The predetermined breaking regions 14, in particular the perforations or indentions, may be produced by geometrically adjusting a mold core. By producing an adjusted mold core with one or more radial protrusions, in particular local radial offsets, a reduced material thickness and, thereby a predetermined breaking region 14, can be produced in the predetermined breaking member 13. The shape and size of the indentations and/or perforations, in particular their radial and axial extensions, the number of indentations and/or perforations and the extension of the predetermined breaking region 14, may be varied.

REFERENCE NUMERALS 1 drug delivery device
2 housing
3 mechanical assembly
4 piston rod
5 distal end of housing
6 dose setting member
7 indicator member
8 thread
9 dose display
10 dose button
11 proximal end
12 threaded insert
13 predetermined breaking member
14 predetermined breaking region
15 spot
16 groove
17 stable region
18 part accommodated in housing
19 distal end of member
20 indication
21 covering material
22 section protruding out of housing
23 outer surface in predetermined breaking region
24 outer surface in stable region

The invention claimed is:

1. A drug delivery device, comprising:
a housing and a mechanical assembly which is at least partially accommodated in the housing, wherein the mechanical assembly comprises a predetermined breaking member which is configured to be damaged when the mechanical assembly or parts thereof are forcefully separated from the housing, wherein the predetermined breaking member comprises a predetermined breaking region in which the predetermined breaking member is configured to be damaged during separation from the housing, and wherein the predetermined breaking region comprises a plurality of spots, each of the spots having a reduced thickness of material or being configured as a perforation, the spots being arranged along a line running helically around a circumference of the predetermined breaking member.

2. The drug delivery device according to claim 1, wherein the predetermined breaking member is configured to prevent a reuse of the drug delivery device.

3. The drug delivery device according to claim 1, wherein the predetermined breaking member is configured to partially protrude out of the housing.

4. The drug delivery device according to claim 1, wherein the predetermined breaking member comprises a thread, wherein the predetermined breaking region is located inside a groove of the thread.

5. The drug delivery device according to claim 1, wherein the predetermined breaking region is configured to be non-visible from outside the drug delivery device.

6. The drug delivery device according to claim 1, wherein the predetermined breaking region is located only near a distal end of the predetermined breaking member.

7. The drug delivery device according to claim 1, wherein an outer surface in the predetermined breaking region is non-discernable from an outer surface in a more stable region of the predetermined breaking member.

8. The drug delivery device according to claim 7, wherein the spots are configured as indentations in an inner surface of the predetermined breaking member.

9. The drug delivery device according to claim 1, comprising a piston rod, wherein the mechanical assembly is configured to drive the piston rod in a distal direction for dispensing a dose of a drug.

10. The drug delivery device according to claim 1, wherein the predetermined breaking member is configured as an indicator member for displaying the size of a dose of a drug to be dispensed.

11. The drug delivery device according to claim 1, wherein the drug delivery device is a pen-type injection device.

12. The drug delivery device according to claim 1, wherein the predetermined breaking member is configured as an indicator member for displaying the size of a dose of a drug to be dispensed and comprises a thread engaged with the housing or a part fixed to the housing, wherein the predetermined breaking region is located inside a groove of the thread and wherein the drug delivery device comprises a stop configured to prevent the predetermined breaking member from being completely drawn out of the housing.

13. A predetermined breaking member for a mechanical assembly of a drug delivery device wherein the predetermined breaking member is configured to be damaged when being forcefully separated from a housing of the drug delivery device, wherein the predetermined breaking member comprises a predetermined breaking region in which the predetermined breaking member is configured to be damaged during separation from the housing, wherein the predetermined breaking region comprises a plurality of spots, each of the spots having a reduced thickness of material or being configured as a perforation, the spots being arranged along a line running helically around a circumference of the predetermined breaking member.

14. The predetermined breaking member according to claim 13, comprising a thread, wherein the predetermined breaking region is located inside a groove of the thread.

15. The predetermined breaking member according to claim 13, wherein the predetermined breaking member is configured as an indicator member for displaying a size of a dose of a drug to be dispensed.

16. A mechanical assembly of a drug delivery device for driving a piston rod, the mechanical assembly comprising a predetermined breaking member configured to be damaged when being forcefully separated from a housing of the drug delivery device, wherein the mechanical assembly is configured to drive the piston rod in a distal direction for dispensing a dose of a drug, wherein the predetermined breaking member comprises a predetermined breaking region in which the predetermined breaking member is configured to be damaged during separation from the housing, wherein the predetermined breaking region comprises a plurality of spots, each of the spots having a reduced thickness of material or being configured as a perforation, the spots being arranged along a line running helically around a circumference of the predetermined breaking member.

* * * * *

UNITED STATES PATENT AND TRADEMARK OFFICE
CERTIFICATE OF CORRECTION

PATENT NO. : 10,933,201 B2
APPLICATION NO. : 15/567625
DATED : March 2, 2021
INVENTOR(S) : Ngoc-Jane Lam Page 1 of 1

It is certified that error appears in the above-identified patent and that said Letters Patent is hereby corrected as shown below:

In the Specification

Column 1, Line 11, delete "in on" and insert -- on --

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*